(12) United States Patent
Levenberg et al.

(10) Patent No.: US 9,861,663 B2
(45) Date of Patent: Jan. 9, 2018

(54) EX-VIVO VASCULARIZED IMPLANT COMPOSITION COMPRISING POLY-L-LACTIC ACID, POLYLACTIC-CO-GLYCOLIC-ACID AND OLFACTORY BULB CELLS

(71) Applicant: TECHNION RESEARCH & DEVELOPMENT FOUNDATION LTD., Haifa (IL)

(72) Inventors: Shulamit Levenberg, Moreshet (IL); Jacob Blumenthal, Kfar Yona (IL)

(73) Assignee: TECHNION RESEARCH & DEVELOPMENT FOUNDATION LTD., Haifa (IL)

(*) Notice: Subject to any disclaimer, the term of this patent is extended or adjusted under 35 U.S.C. 154(b) by 0 days.

(21) Appl. No.: 13/775,556

(22) Filed: Feb. 25, 2013

(65) Prior Publication Data
US 2013/0236503 A1 Sep. 12, 2013

Related U.S. Application Data

(60) Provisional application No. 61/602,138, filed on Feb. 23, 2012.

(51) Int. Cl.
| | |
|---|---|
| C12N 5/00 | (2006.01) |
| C12N 5/079 | (2010.01) |
| C12N 5/0793 | (2010.01) |
| C12N 5/071 | (2010.01) |
| C12N 5/16 | (2006.01) |
| C12N 5/0735 | (2010.01) |
| C12N 5/074 | (2010.01) |
| A61K 35/33 | (2015.01) |
| A61K 35/30 | (2015.01) |
| A61K 35/44 | (2015.01) |
| A61L 27/18 | (2006.01) |
| A61L 27/34 | (2006.01) |
| A61L 27/38 | (2006.01) |
| A61L 27/54 | (2006.01) |
| A61L 27/56 | (2006.01) |

(52) U.S. Cl.
CPC .............. *A61K 35/33* (2013.01); *A61K 35/30* (2013.01); *A61K 35/44* (2013.01); *A61L 27/18* (2013.01); *A61L 27/34* (2013.01); *A61L 27/383* (2013.01); *A61L 27/3804* (2013.01); *A61L 27/3808* (2013.01); *A61L 27/3886* (2013.01); *A61L 27/54* (2013.01); *A61L 27/56* (2013.01); *A61L 2300/414* (2013.01)

(58) Field of Classification Search
CPC .............. A61F 2/062; A61F 2240/001; A61F 2400/001; G01N 33/5008; G01N 33/5088; B01L 2200/12; B29K 2995/0056; B29K 2995/006; B29L 2009/00; B29L 2023/00; C12N 5/0602; C12N 5/0697; C12Q 1/00; C12Q 1/008; A61L 27/34; A61L 2300/414; A61L 27/3804; A61L 27/3808; A61L 27/383; A61L 27/3886; A61L 27/54; A61L 27/56; A61L 7/3804; C08L 67/04; C08L 89/00; C08L 2200/12; C12M 25/14; A61K 35/30; A61K 35/33; A61K 35/44

See application file for complete search history.

(56) References Cited

U.S. PATENT DOCUMENTS

| | | | | |
|---|---|---|---|---|
| 7,670,797 | B2 * | 3/2010 | Vacanti | C12Q 1/00 435/30 |
| 7,838,292 | B1 * | 11/2010 | Roisen et al. | 435/377 |
| 8,067,237 | B2 * | 11/2011 | Mooney et al. | 435/375 |
| 8,147,562 | B2 * | 4/2012 | Vacanti | C12M 25/14 137/803 |
| 8,173,361 | B2 * | 5/2012 | Vacanti | C12Q 1/00 435/4 |
| 8,329,166 | B2 * | 12/2012 | Li et al. | 424/93.7 |
| 8,367,410 | B2 * | 2/2013 | Radisic | C12N 5/0658 435/173.1 |
| 8,591,597 | B2 * | 11/2013 | Hoganson | A61F 2/062 623/1.42 |
| 8,734,759 | B2 * | 5/2014 | Hornstein et al. | 424/9.1 |
| 8,951,302 | B2 * | 2/2015 | Pryor | G01N 33/5008 623/23.65 |
| 2002/0127716 | A1 * | 9/2002 | Feron et al. | 435/368 |
| 2003/0006534 | A1 * | 1/2003 | Taboas | A61F 2/30756 264/401 |
| 2003/0121064 | A1 * | 6/2003 | Logan et al. | 800/8 |
| 2005/0112759 | A1 * | 5/2005 | Radisic | C12N 5/0658 435/366 |
| 2005/0271631 | A1 * | 12/2005 | Lee | A61K 38/363 424/93.7 |
| 2006/0019326 | A1 * | 1/2006 | Vacanti | C12Q 1/00 435/18 |

(Continued)

OTHER PUBLICATIONS

ECM gel datasheet from Sigma online catalogue, retrieved from the sigma website on Nov. 2, 2013.*
Williams et al. Nature 1991; 352:438-441.*
Woodhall et al. Mol. Brain Res. 2001; 88:203-213.*
Qian et al. Chin. Med. J. 2009; 122:2032-40.*
Wang et al. Neurosci. Lett., 2006; 401:65-70.*
Lesman et al. Biomaterials, 2011; 32:7856-7869, available online Aug 4, 2011.*
Novosel eta l. Adv. Drug Delivery Rev. 2011; 63:300-311.*
Nash eta l. Glia 2001; 34:81-87.*
Blumenthal et al., Tissue Engineering 2013; 19:2284-2291.*
Barnett et al. Chapter 8 of the book: Neural Stem Cells: Methods and Protocols, 2nd edition, edited by Leslie p. Weiner, 2008, Humana Press.*

(Continued)

*Primary Examiner* — Chang-Yu Wang
(74) *Attorney, Agent, or Firm* — The Roy Gross Law Firm, LLC; Roy Gross

(57) ABSTRACT

The present invention provides a composition including a poly-l-lactic acid (PLLA) and polylactic-co-glycolic-acid (PLGA) scaffold on which neuronal tissue is grown ex-vivo. Furthermore, the invention provides a method for making ex-vivo cellular vasculature networks, and a method for treating a neuronal injury in a subject by implanting the current composition.

13 Claims, 7 Drawing Sheets

(56) References Cited

U.S. PATENT DOCUMENTS

| | | | |
|---|---|---|---|
| 2006/0019389 A1* | 1/2006 | Yayon | A01N 1/02 435/395 |
| 2006/0136182 A1* | 6/2006 | Vacanti | C12M 25/14 703/11 |
| 2006/0172008 A1* | 8/2006 | Yayon | A61K 9/0024 424/488 |
| 2007/0141035 A1* | 6/2007 | Li et al. | 424/93.7 |
| 2007/0280989 A1* | 12/2007 | Shahar et al. | 424/423 |
| 2007/0286880 A1* | 12/2007 | Vasiliev | A61K 35/36 424/422 |
| 2008/0044900 A1* | 2/2008 | Mooney et al. | 435/375 |
| 2010/0136114 A1* | 6/2010 | Mao | A61K 35/44 424/486 |
| 2010/0234678 A1* | 9/2010 | Pryor | G01N 33/5008 600/36 |
| 2010/0274353 A1* | 10/2010 | Pryor | G01N 33/5008 623/1.42 |
| 2011/0008765 A1* | 1/2011 | Vacanti | C12Q 1/00 435/5 |
| 2011/0014695 A1* | 1/2011 | Roisen et al. | 435/368 |
| 2011/0014701 A1* | 1/2011 | Ghosh | C12N 5/0663 435/374 |
| 2012/0134967 A1* | 5/2012 | Mooney et al. | 424/93.7 |
| 2013/0115694 A1* | 5/2013 | Hickman et al. | 435/347 |
| 2014/0050766 A1* | 2/2014 | Levenberg | A61L 27/225 424/400 |
| 2014/0081384 A1* | 3/2014 | Hoganson | A61F 2/062 623/1.27 |
| 2014/0087466 A1* | 3/2014 | Ligler | C12N 5/0697 435/400 |
| 2016/0193382 A1* | 7/2016 | Levenberg | A61L 27/18 424/423 |

OTHER PUBLICATIONS

Carletti E, Motia A, and Migliaresi C. Scaffolds for tissue engineering and 3D cell culture. Methods Mol Biol. 2011; 695:17-39.

Doucette R. Glial cells in the nerve fiber layer of the main olfactory bulb of embryonic and adult mammals, Microsc Res Tech. 24:113-30. 1993.

Farbman Al. Olfactory neurogenesis: genetic or environmental controls? Trends Neurosci.13:362-5. 1990.

Irrialzumi T, Lankford KL, Waxman SG, Greer CA, Kocsis JD. Transplanted olfactory ensheathing cells remyelinate and ehance axonal conduction in the demyelinated dorsal columns of the rat spinal cord. J Neurosci. 18:6176-85. 1998.

Joni HR, Raisman G. Ensheathing cell cultures from the olfactory bulb and mucosa. Glia.47:130-7. 2004.

Li (2009) PLGA conduit seeded with olfactory ensheathing cells for bridging sciatic nerve cetecl of rats.

Lipson AC, Widenfalk J, Lindqvist E, Ebendal T, Olson L. Neurotrophic properties of olfactory ensheathing glia. Exp Neurol. 180:167-71. 2003.

Moreno-Flores MT, Diaz-Nido J, Wandosell F, Avila J. Olfactory Ensheathing Glia: Drivers of Axonal Regeneration in the Central Nervous System? J Biomed Biotechnol.2:37-43. 2002.

Ramon-Cueto A, Nieto-Sampedri M. Regeneration into the spinal cord of transected dorsal root axons is promoted by ensheathing glia transplants. Exp Neurol.127:232-44. 1994.

Richter M, Westendorf K, Roskams AJ. Culturing olfactory ensheathing cells from the mouse olfactory epithelium. Methods Mol Biol. 438:95-102. 2008.

Shoufeng Yang, Kah-Fai Leong, Zhaohui Du, and Chee-Kai Chua,. The Design of Scaffolds for Use in Tissue Engineering. Part I. Traditional Factors. Tissue Engineering vol. 7 No. 6, 2001.

Woodhall E, West AK, Chuah MI. Cultured olfactory ensheathing cells express nerve growth factor, brain-derived neurotrophic factor, glia cell line-derived neurotrophic factor and their receptors. Brian Res Mol Brain Res.88:203-13. 2001.

* cited by examiner

EX-VIVO VASCULARIZED IMPLANT COMPOSITION COMPRISING POLY-L-LACTIC ACID, POLYLACTIC-CO-GLYCOLIC-ACID AND OLFACTORY BULB CELLS

FIELD OF INVENTION

This invention is directed to; inter alia, scaffolds for generating a neuronal tissue and to methods for treating neuronal injuries by implanting the scaffolds on which neuronal tissue was grown.

BACKGROUND OF THE INVENTION

In the United States alone, approximately 25% of patients in need of organ transplants die while waiting for a suitable donor. The current demands for transplant organs and tissues are far outpacing the supply, and all manner of projections indicate that this gap will continue to widen. Cell transplantation was proposed as an alternative treatment to whole organ transplantation for failing or malfunctioning organs. For the creation of an autologous implant, donor tissue is harvested and dissociated into individual cells, and the cells are attached and cultured onto a proper substrate that is ultimately implanted at the desired site of the functioning tissue. Because many isolated cell populations can be expanded in-vitro using cell culture techniques, only a very small number of donor cells may be necessary to prepare such implants. However, it is believed that isolated cells cannot form new tissues, independently. Most primary organ cells are believed to be anchorage-dependent and require specific environments that very often include the presence of a supporting material to act as a template for growth. The success of any cell transplantation therapy therefore relies on the development of suitable substrates for both in-vitro and in-vivo tissue culture. Currently, these substrates, mainly in the form of tissue engineering scaffolds, prove less than ideal for applications, not only because they lack mechanical strength, but they also suffer from a lack of interconnection channels (Shoufeng Yang, Kah-Fai Leong, Zhaohui Du, and Chee-Kai Chua. The Design of Scaffolds for Use in Tissue Engineering. Part I. Traditional Factors. Tissue Engineering Vol. 7 No. 6, 2001).

Tissue engineering applications or even in 3D cell cultures, the biological cross talk between cells and the scaffold is controlled by the material properties and scaffold characteristics. In order to induce cell adhesion, proliferation, and activation, materials used for the fabrication of scaffolds must possess requirements such as intrinsic biocompatibility and proper chemistry to induce molecular bio-recognition from cells. Materials, scaffold mechanical properties and degradation kinetics should be adapted to the specific tissue engineering application to guarantee the required mechanical functions and to accomplish the rate of the new-tissue formation. For scaffolds, pore distribution, exposed surface area, and porosity play a major role, whose amount and distribution influence the penetration and the rate of penetration of cells within the scaffold volume, the architecture of the produced extracellular matrix, and for tissue engineering applications, the final effectiveness of the regenerative process. Depending on the fabrication process, scaffolds with different architecture can be obtained, with random or tailored pore distribution. In the recent years, rapid prototyping computer-controlled techniques have been applied to the fabrication of scaffolds with ordered geometry (Carletti E, Motta A, and Migliaresi C. Scaffolds for tissue engineering and 3D cell culture. Methods Mol Biol. 2011; 695:17-39).

Since the publication of Cajal's pioneering studies, it has been clear that neurons from the central nervous system (CNS) regenerate poorly, in contrast to those from the peripheral nervous system (PNS). Throughout adult life, olfactory sensory neurons are continuously replenished from progenitor cells of the olfactory neuroepithelium. Furthermore, unlike other peripheral nervous system (PNS) neurons, these neurons extend axons that reach their final targets in the central nervous system (CNS)-situated olfactory bulb (OB) (Farbman A I. Olfactory neurogenesis: genetic or environmental controls? Trends Neurosci. 13:362-5. 1990; Doucette R. Glial cells in the nerve fiber layer of the main olfactory bulb of embryonic and adult mammals. Microsc Res Tech. 24:113-30. 1993).

Olfactory ensheathing cells (OECs) are a unique glial cell type that resides in the olfactory bulb and in the olfactory mucosa (Richter M, Westendorf K, Roskams A J. Culturing olfactory ensheathing cells from the mouse olfactory epithelium. Methods Mol Biol. 438:95-102. 2008; Jani H R, Raisman G. Ensheathing cell cultures from the olfactory bulb and mucosa. Glia. 47:130-7. 2004). OECs envelop olfactory sensory axons along their way to the target neurons in the olfactory bulb. Thus, OECs have drawn much attention with respect to CNS axonal regeneration (Moreno-Flores M T, Diaz-Nido J, Wandosell F, Avila J. Olfactory Ensheathing Glia: Drivers of Axonal Regeneration in the Central Nervous System? J Biomed Biotechnol. 2:37-43. 2002) and have been proposed to facilitate this process in the injured CNS (Ramon-Cueto A, Nieto-Sampedro M. Regeneration into the spinal cord of transected dorsal root axons is promoted by ensheathing glia transplants. Exp Neurol. 127: 232-44. 1994). Indeed, the regenerative capacity of these cells in the injured spinal cord and their ability to remyelinate injured spinal cord axons has been confirmed in several studies (Imaizumi T, Lankford K L, Waxman S G, Greer C A, Kocsis J D. Transplanted olfactory ensheathing cells remyelinate and enhance axonal conduction in the demyelinated dorsal columns of the rat spinal cord. J Neurosci. 18:6176-85. 1998). OECs have been suggested to support axon growth in the injured CNS via expression of growth factors, such as NGF, NT4/5, NT3, and BDNF (Lipson A C, Widenfalk J, Lindqvist E, Ebendal T, Olson L. Neurotrophic properties of olfactory ensheathing glia. Exp Neurol. 180: 167-71. 2003; Woodhall E, West A K, Chuah M I. Cultured olfactory ensheathing cells express nerve growth factor, brain-derived neurotrophic factor, glia cell line-derived neurotrophic factor and their receptors. Brain Res Mol Brain Res. 88:203-13. 2001).

SUMMARY OF THE INVENTION

In one embodiment, the present invention provides a composition comprising: A) a porous sponge, B) culture medium, C) nerve growth factor (NGF), D) olfactory bulb cells, and E) fibronectin, wherein the porous sponge comprises poly-l-lactic acid (PLLA) and polylactic-co-glycolic-acid (PLGA), wherein NGF is produced by the olfactory bulb cells in the composition, wherein the porous sponge comprises pores having a diameter of 150-800 μm, wherein the pores comprise the olfactory bulb cells, and wherein the olfactory bulb cells are attached to the surface of the porous sponge and attached within the porous sponge. In another embodiment, the sole source of NGF is OBC secretion of NGF within the composition of the invention.

In another embodiment, the present invention further provides that the olfactory bulb cells express the NGF receptor p75NTR. In another embodiment, the present invention further provides that olfactory bulb cells have neurite extensions. In another embodiment, the present invention further provides that the porous sponge comprises at least 85% porosity. In another embodiment, the present invention further provides that the composition further comprises endothelial cells, fibroblasts, and vasculature networks. In another embodiment, the present invention further provides that the composition is cultured for at least 14 days.

In another embodiment, the present invention further provides a method for making cellular vasculature networks, comprising the step of co-culturing olfactory bulb cells and fibroblasts and/or endothelial cells in a composition such as described herein, wherein the olfactory bulb cells and the fibroblasts and/or endothelial cells are grown on the scaffold of the invention.

In another embodiment, the present invention further provides a method for treating a neuronal injury in a subject, comprising the step of implanting the composition such as described herein, in a site of neuronal injury, thereby treating a neuronal injury in a subject.

DETAILED DESCRIPTION OF THE INVENTION

Figure 1:
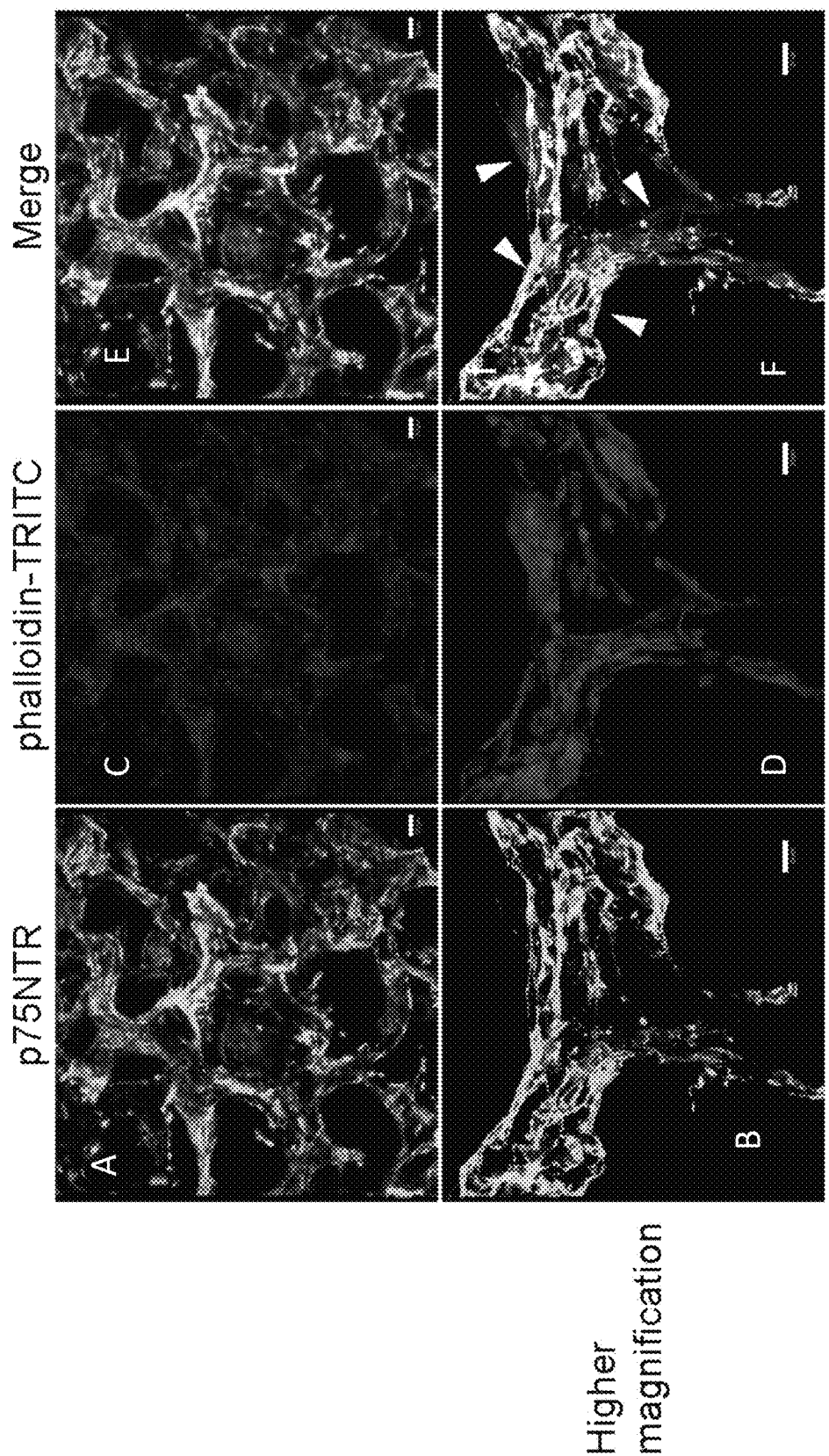
FIG. 1: Micrographs showing OECs grown on 3D scaffolds. OB-derived OECs were seeded and cultured on PLLA/PLGA scaffolds prior to immunofluorescence analysis with Phalloidin TRITC (C and D) to identify OB cells (gray, white arrows) and a p75NTR (A and B) antibody to identify OECs (dark gray, light gray arrows). Merge stainings is provided in E and F. A, C, and E: confocal analysis at low magnification (scale bar=50 µm). B, D, and F: higher magnification. Scale bar=20 µm.

In one embodiment, the present invention provides a composition comprising: A) a porous sponge (scaffold), B) culture medium, C) nerve growth factor (NGF), D) olfactory bulb cells (OBC) attached to the porous sponge, and E) fibronectin, wherein the porous sponge comprises poly-l-lactic acid (PLLA) and polylactic-co-glycolic-acid (PLGA), and wherein NGF is produced by the olfactory bulb cells attached to the scaffold and/or within the composition. In another embodiment, the present invention provides that the porous sponge provides a 3D tissue culture scaffold. In another embodiment, the sole source of NGF in the composition of the invention is OBC production and secretion during culturing with the 3D scaffold as described herein.

In another embodiment, the present invention provides a bioactive scaffold composition such that the bioactive scaffold composition controls the growth of a bioactive regenerative five nerve tissue. In another embodiment, the present invention provides a bioactive scaffold composition that further supports de-novo, in-vivo neuronal tissue growth at a site of implantation.

In another embodiment, the composition comprises a scaffold. In another embodiment, the scaffold is a porous sponge. In another embodiment, the sponge is devoid of an organized structure, layer, or network of layers. In another embodiment, the composition is devoid of any layer of aligned fibers. In another embodiment, the scaffold is devoid of any layer of aligned fibers. In another embodiment, the composition is devoid of curved fibers. In another embodiment, the scaffold is devoid of curved fibers.

In another embodiment, a porous sponge comprises at least 50% porosity. In another embodiment, a porous sponge comprises at least 60% porosity. In another embodiment, a porous sponge comprises at least 70% porosity. In another embodiment, a porous sponge comprises at least 75% porosity. In another embodiment, a porous sponge comprises at least 80% porosity. In another embodiment, a porous sponge comprises at least 85% porosity. In another embodiment, a porous sponge comprises at least 90% porosity. In another embodiment, a porous sponge comprises at least 92% porosity. In another embodiment, a porous sponge comprises at least 95% porosity.

In another embodiment, a porous sponge comprises pores having a diameter of at least 100 µm. In another embodiment, a porous sponge comprises pores having a diameter of at least 120 µm. In another embodiment, a porous sponge comprises pores having a diameter of at least 150 µm. In another embodiment, a porous sponge comprises pores having a diameter of 100-900 µm. In another embodiment, a porous sponge comprises pores having a diameter of 120-900 µm. In another embodiment, a porous sponge comprises pores having a diameter of 120-850 µm. In another embodiment, a porous sponge comprises pores having a diameter of 150-800 µm. In another embodiment, a porous sponge comprises pores having a diameter of 200-800 µm. In another embodiment, a porous sponge comprises pores having a diameter of 220-750 µm.

In another embodiment, olfactory bulb cells (OBC) is a mixture of different cell types. In another embodiment, olfactory bulb cells are derived from the olfactory bulb. In another embodiment, olfactory bulb cells comprise fibroblasts, astrocytes and olfactory ensheathing cells (OECs). In another embodiment, olfactory ensheathing cells (OECs) are a distinctive type of glia that secrete neurotrophic factors and form myelin sheaths around axons projecting from the olfactory mucosa into the central nervous system olfactory bulb.

In another embodiment, olfactory bulb-derived cells seeded on 3D scaffolds of the invention exhibit neurotrophic factor expression and pro-angiogenic properties. In another embodiment, the expression of BDNF and NGF genes in cells grown on 3D scaffolds compared to 2D monolayer cultures was significantly upregulated by at least 2 fold, 3 fold, 4 fold, 5 fold, 6 fold, 8 fold, or by at least 10 fold.

In another embodiment, olfactory bulb cells occupy the scaffold in all three dimensions. In another embodiment, any cell mentioned herein occupies the scaffold in all three dimensions. In another embodiment, olfactory bulb cells occupy the pores. In another embodiment, an olfactory bulb cell resides within a pore. In another embodiment, an olfactory bulb cell resides on the scaffold's surface. In another embodiment, olfactory bulb cells are present both within the pores and on the scaffold's surface.

In another embodiment, cells are syngeneic cells. In another embodiment, cells are allogeneic cells.

In another embodiment, olfactory bulb cells express the NGF receptor p75NTR. In another embodiment, an olfactory bulb cell within a pore expresses the NGF receptor p75NTR. In another embodiment, olfactory bulb cells express Neurog2. In another embodiment, olfactory bulb cells express NeuN.

In another embodiment, the present invention further provides that the composition is cultured for at least 14 days. In another embodiment, the composition described herein comprises both poly-l-lactic acid (PLLA) and polylactic-co-glycolic-acid (PLGA). In another embodiment, the scaffold described herein comprises both poly-l-lactic acid (PLLA) and polylactic-co-glycolic-acid (PLGA). In another embodiment, PLLA and PLGA are in 1:3 to 3:1 w/w ratio. In another embodiment, PLLA and PLGA are in 1:2 to 2:1 w/w ratio. In another embodiment, PLLA and PLGA are in 1:1.5 to 1.5:1 w/w ratio. In another embodiment, PLLA and PLGA are in 1:1 w/w ratio.

In another embodiment, the composition described herein further comprises endothelial cells such as human umbilical vein endothelial cells (HUVEC), fibroblasts such as human foreskin fibroblasts (HFF) or both. In another embodiment, HUVEC and/or HFF are attached to the scaffold. In another embodiment, the presence of olfactory bulb cells and HUVEC on a single scaffold results in the formation of vasculature networks. In another embodiment, the presence of olfactory bulb cells and HFF on a single scaffold results in the formation of vasculature networks. In another embodiment, the presence of olfactory bulb cells, HUVEC and HFF on a single scaffold results in the formation of vasculature networks. In another embodiment, olfactory bulb cells induce HUVEC and/or HFF to form vasculature network. In another embodiment, cells attached to a scaffold such as described herein comprise neurite extensions. In another embodiment, OBC attached to a scaffold such as described herein comprises neurite extensions.

In another embodiment, a cell is attached to a scaffold such as described herein for at least 10 days. In another embodiment, a cell is attached to a scaffold such as described herein for at least 14 days. In another embodiment, a cell is attached to a scaffold such as described herein for 10 to 21 days. In another embodiment, a cell is attached to a scaffold such as described herein for 14 to 31 days. In another embodiment, an olfactory bulb cell is attached to a scaffold for at least 14 days.

In another embodiment, a porous sponge-scaffold of the invention is further coated with a polymer. In another embodiment, a porous sponge-scaffold of the invention is further coated with an extracellular matrix protein. In another embodiment, a porous sponge-scaffold of the invention is further coated with fibronectin. In another embodiment, a porous sponge-scaffold of the invention is further coated with polypyrrole. In another embodiment, a porous sponge-scaffold of the invention is further coated with polycaprolactone. In another embodiment, a porous sponge-scaffold of the invention is further coated with poly(ethersulfone). In another embodiment, a porous sponge-scaffold of the invention is further coated with poly(acrylonitrile-co-methylacrylate) (PAN-MA). In another embodiment, a porous sponge-scaffold of the invention further comprises a chemoattractant such as but not limited to laminin-1.

In another embodiment, a composition as described herein further comprises fibrin. In another embodiment, a composition as described herein further comprises thrombin.

In another embodiment, a scaffold such as described herein is 10-160 mm$^3$. In another embodiment, a scaffold such as described herein is 10-80 mm$^3$. In another embodiment, a scaffold such as described herein is 15-50 mm$^3$. In another embodiment, a scaffold such as described herein is a square. In another embodiment, a scaffold such as described herein is a rectangle.

In another embodiment, the three three-dimensional scaffolds described herein can further include a therapeutic agent. In another embodiment, the therapeutic agent can be any therapeutic agent. In another embodiment, the therapeutic agent can be a polypeptide, polypeptide fragment, nucleic acid molecule, small molecule, ribozyme, shRNA, RNAi, antibody, antibody fragment, scFv, enzyme, carbohydrate, or any combination thereof. In some embodiments, the therapeutic agent can be brain-derived neurotrophic factor (BDNF), neurotrophic 3 (NT3), nerve growth factor (NGF), or glial cell-line derived neurotrophic factor (GNDF). The therapeutic agent, in some embodiments, is chondroitinase ABC (chABC) or sialidase. The three-dimensional scaffold can release, in one embodiment, the therapeutic agent for at least 1 day, 1 week, or 1 month.

In another embodiment, the scaffold includes a cellular substrate. In another embodiment, the cellular substrate is any cellular substrate. In embodiments, the cellular substrate is a Schwann cell, an oligodendrocyte, an olfactory ensheathing glia (OEG), an oligodendrocyte progenitor cell (OPC), an embryonic stem cell (ESc), an adult stem cell, an induced pluripotent stem cell, a differentiated ESc and differentiated adult Stem cell, an induced pluripotent Stem cell (iPSc), and a macrophage.

In another embodiment, a composition as described herein further comprises a material selected from the group consisting of collagen-GAG, collagen, fibrin, PLA, PGA, PLA-PGA co-polymer, poly(anhydride), poly(hydroxy acid), poly(ortho ester), poly(propylfumerate), poly(caprolactone), polyamide, polyamino acid, polyacetal, biodegradable polycyanoacrylate, biodegradable polyurethane and polysaccharide, polypyrrole, polyaniline, polythiophene, polystyrene, polyester, nonbiodegradable polyurethane, polyurea, poly(ethylene vinyl acetate), polypropylene, polymethacrylate, polyethylene, polycarbonate and poly(ethylene oxide).

In another embodiment, a composition as described herein is cultured for at least 14 days in-vitro, in order to reach baseline proliferation rates.

In another embodiment, a composition as described herein further comprises a cell adhesion promoting agent, a proliferation inducer, a differentiation inducer, an extravasation inducer and/or a migration inducer. In another embodiment, a composition as described herein further comprises a cell adhesion protein, a growth factor, a cytokine, a hormone, a protease a protease substrate, or any combination thereof. In another embodiment, any substance as described herein is attached to the scaffold. In another embodiment, any substance as described herein is embedded within the scaffold. In another embodiment, any substance as described herein is impregnated within the scaffold. In another embodiment, a scaffold such as described herein is coated with a gel. In another embodiment, a scaffold such as described herein is biodegradable.

In another embodiment, the porosity of the scaffold is controlled by a variety of techniques known to those skilled in the art. In another embodiment, as the porosity is increased, use of polymers having a higher modulus, addition of suffer polymers as a co-polymer or mixture, or an increase in the cross-link density of the polymer are used to increase the stability of the scaffold with respect to cellular contraction.

In another embodiment, the choice of polymer and the ratio of polymers in a co-polymer scaffold of the invention is adjusted to optimize the stiffness/porosity of the scaffold. In another embodiment, the molecular weight and cross-link density of the scaffold is regulated to control both the mechanical properties of the scaffold and the degradation rate (for degradable scaffolds). In another embodiment, the mechanical properties are optimized to mimic those of the tissue at the implant site. In another embodiment, the shape and size of the final scaffold are adapted for the implant site and tissue type. In another embodiment, scaffold materials comprise natural or synthetic organic polymers that can be gelled, or polymerized or solidified (e.g., by aggregation, coagulation, hydrophobic interactions, or cross-linking) into a 3-D open-lattice structure that entraps water and/or other molecules, e.g., to form a hydrogel.

In another embodiment, polymers used in scaffold material compositions are biocompatible, biodegradable and/or bioerodible and act as adhesive substrates for cells. In another embodiment, the structural scaffold materials are non-resorbing or non-biodegradable polymers or materials. The phrase "non-biodegradable polymer", as used herein, refers to a polymer or polymers which at least substantially (i.e. more than 50%) do not degrade or erode in-vivo. The terms "non-biodegradable" and "non-resorbing" are equivalent and are used interchangeably herein.

In another embodiment, the phrase "biodegradable polymer" as used herein, refers to a polymer or polymers which degrade in-vivo, and wherein erosion of the polymer or polymers over time occurs concurrent with or subsequent to release of cells/tissue. The terms "biodegradable" and "bio-erodible" are equivalent and are used interchangeably herein.

In another embodiment, scaffold materials comprise naturally occurring substances, such as, fibrinogen, fibrin, thrombin, chitosan, collagen, alginate, poly(N-isopropylacrylamide), hyaluronate, albumin, collagen, synthetic polyamino acids, prolamines, polysaccharides such as alginate, heparin, and other naturally occurring biodegradable polymers of sugar units. In another embodiment, structural scaffold materials are ionic hydrogels, for example, ionic polysaccharides, such as alginates or chitosan. Ionic hydrogels may be produced by cross-linking the anionic salt of alginic acid, a carbohydrate polymer isolated from seaweed, with ions, such as calcium cations.

In another embodiment, the scaffolds of the invention are made by any of a variety of techniques known to those skilled in the art. Salt-leaching, porogens, solid-liquid phase separation (sometimes termed freeze-drying), and phase inversion fabrication are used, in some embodiments, to produce porous scaffolds.

As used herein, "transplanting" refers to providing the scaffold supported cells of the present invention, using any suitable route. Typically, the scaffold supported cells are administered by injection using a catheter.

In another embodiment, a culture medium comprises DMEM/F12, Nutrient Mix and 7-15% fetal bovine serum. In another embodiment, a culture medium comprises Neurobasal-A (Invitrogen). In another embodiment, a culture medium comprises 0.5-1.2 mM L-glutamine. In another embodiment, a culture medium comprises 0.1-0.8% methylcellulose. In another embodiment, a culture medium comprises 5-15 mM HEPES. In another embodiment, a culture medium has a pH of 7.2-7.8. In another embodiment, a culture medium has a pH of 7.4-7.6. In another embodiment, a culture medium comprises 2-8 µg/ml Gentamycin. In another embodiment, a culture medium comprises B27-supplement. In another embodiment, a culture medium comprises L-15 medium (Invitrogen). In another embodiment, a culture medium is any medium provided in: Ronald Doucette. Protocols for Neural Cell Culture (2001) which is incorporated herein by reference in its entirety. In another embodiment, a culture medium is any medium provided in: Doucette, 1984, Doucette, 1986, 11,1; Raisman, 1985; Li et al., 1997; Perez-Bouza et al., 1998; Ramon-Cueto and Nieto-Sampedro, 1994; Ramon-Cueto et al., 1998; Smale et al., 1996; Franklin et al., 1996; Imaizumi et al., 1998; Doucette, 1990; Doucette, 1995; Franklin and Barnett, 1997; Ramon-Cueto and Avila, 1998; Ramon-Cueto and Valverde, 1995 which are incorporated herein by reference in their entireties.

In another embodiment, the present invention provided that OB-derived cells promotes the formation of dense, HUVEC-rich networks of thin vessel-like structures on scaffolds (data not shown), further highlighting the supportive features of OB-derived cells for injury repair. In another embodiment, the present invention further provides a method for making cellular vasculature networks, comprising the step of co-culturing olfactory bulb cells and endothelial cells in a composition such as described herein, wherein the olfactory bulb cells and the endothelial cells are grown on the scaffold of the invention. In another embodiment, OB-derived cells stimulated network formation of endothelial cells grown on the same scaffolds. In another embodiment, 3D scaffolds of the invention maintained and strengthened the unique therapeutic properties of embedded OB-derived cells. In another embodiment, the present invention provided that OB-derived cells stimulate organization of endothelial cells into de-novo vasculature networks and thus attracting vascular networks into the spinal cord injury lesion site. In another embodiment, the present invention provided that OB-derived cells grown on the 3D scaffold of the invention, highly expressed neurotrophic factors, which then modulated neuronal survival and differentiation. In another embodiment, OB-derived cells grown on 3D scaffolds supported angiogenic behavior, including formation of endothelial cell-based vessel-like networks. In another embodiment, the 3D PLLA/PLGA scaffolds dramatically and unexpectedly increased the therapeutic potential of OB-derived cells for transplantation in patients afflicted with pathologies such as: SCI.

In another embodiment, the present invention further provides a method for making cellular vasculature networks, comprising the step of co-culturing olfactory bulb cells and fibroblasts in a composition such as described herein, wherein the olfactory bulb cells and the fibroblasts are grown on the scaffold of the invention. In another embodiment, the present invention further provides a method for making cellular vasculature networks, comprising the step of co-culturing olfactory bulb cells, endothelial cells, and fibroblasts in a composition such as described herein, wherein the olfactory bulb cells, endothelial cells, and the fibroblasts are grown on the scaffold of the invention. In another embodiment, endothelial cells are HUVEC. In another embodiment, fibroblasts are HFF. In another embodiment, a method for making cellular vasculature networks is a method of ex-vivo vascularizing. In another embodiment, a method for making cellular vasculature networks is a method of ex-vivo vascularizing a neuronal 3D cell culture within a scaffold. In another embodiment, a method for making cellular vasculature networks is a method of ex-vivo vascularizing a neuronal 3D de-novo tissue culture within a scaffold. In another embodiment, a method for making cellular vasculature networks comprises in-vitro culturing the cells within the scaffold for a period of at least 1 week. In another embodiment, a method for making cellular vasculature networks comprises in-vitro culturing the cells within the scaffold for a period of at least 10 days. In another embodiment, a method for making cellular vasculature networks comprises in-vitro culturing the cells within the scaffold for a period of at least 14 days.

In another embodiment, the invention further provides a method for neuro-regeneration. In another embodiment, the present invention relates to the regeneration, reconstruction, repair, augmentation or replacement of a damaged nerve tissue or structure using scaffolds comprising cells as described herein.

In another embodiment, the invention provides a regenerative cell population containing at least one regenerative cell that when deposited on a scaffold as described herein and implanted into a subject in need (a subject afflicted with neuronal injury), provides a regenerative effect for the damaged neuronal tissue that is the subject of the reconstruction, repair, augmentation, or replacement contemplated herein. In another embodiment, the invention provides that OBC is a regenerative cell population that has the ability to stimulate or initiate regeneration of a nerve tissue upon implantation into a patient in need. In general, the regeneration of an organ or tissue structure is characterized by the restoration of cellular components, tissue organization and architecture, function, and regulative development. In addition, an OBC regenerative cell population grown on a scaffold as described herein minimizes the incompleteness or disorder that tends to occur at the implantation site. In another embodiment, disorganization at the site of implantation can manifest itself as increased collagen deposition and/or scar tissue formation, each of which can be minimized through the use of a composition as described herein.

In another embodiment, the invention further provides a method for treating a neuronal injury in a subject, comprising the step of implanting the composition of the invention at a site of neuronal injury, thereby treating a neuronal injury in a subject. In another embodiment, the invention further provides a method for treating a neuronal injury in a subject, comprising the step of implanting a scaffold comprising the cells of the invention at a site of neuronal injury, thereby treating a neuronal injury in a subject. In another embodiment, a scaffold comprising cells such as described herein is implanted in a lesion cavity. In another embodiment, soluble neurotrophic factors are further administered at the implantation site. In another embodiment, neuronal injury is a peripheral nerve injury. In another embodiment, neuronal injury is a CNS injury. In another embodiment, neuronal injury is a spinal cord injury.

In another embodiment, a scaffold comprising cells such as described herein supports neuronal survival and regeneration after spinal cord injury. In another embodiment, a subject described herein is further treated with BDNF, NT-3, and/or VEGF.

In another embodiment, the scaffold to be implanted in a subject suffering from a neuronal injury comprises vasculature networks. In another embodiment, the scaffold to be implanted in a subject suffering from a neuronal injury comprises OBC and endothelial cells. In another embodiment, the scaffold to be implanted in a subject suffering from a neuronal injury comprises OBC and fibroblasts. In another embodiment, the scaffold to be implanted in a subject suffering from a neuronal injury comprises OBC, endothelial cells, and fibroblasts. In another embodiment, the scaffold to be implanted in a subject suffering from a neuronal injury comprises cells having neurite extensions.

The phrase "treating" refers to inhibiting or arresting the development of a disease, disorder or condition and/or causing the reduction, remission, or regression of a disease, disorder or condition in an individual suffering from, or diagnosed with, the disease, disorder or condition. Those of skill in the art will be aware of various methodologies and assays which can be used to assess the development of a disease, disorder or condition, and similarly, various methodologies and assays which can be used to assess the reduction, remission or regression of a disease, disorder or condition.

As used herein, the singular forms "a", "an", and "the" include plural forms unless the context clearly dictates otherwise. Thus, for example, reference to "a therapeutic agent" includes reference to more than one therapeutic agent.

Unless specifically stated or obvious from context, as used herein, the term "or" is understood to be inclusive.

The term "including" is used herein to mean, and is used interchangeably with, the phrase "including but not limited to".

As used herein, the terms "comprises," "comprising," "containing," "having" and the like can have the meaning ascribed to them in U.S. patent law and can mean "includes," "including," and the like; "consisting essentially of" or "consists essentially" likewise has the meaning ascribed in U.S. patent law and the term is open-ended, allowing for the presence of more than that which is recited so long as basic or novel characteristics of that which is recited is not changed by the presence of more than that which is recited, but excludes prior art embodiments.

The term "subject" or "patient" refers to an animal which is the object of treatment, observation, or experiment. By way of example only, a subject includes, but is not limited to, a mammal, including, but not limited to, a human or a non-human mammal, such as a non-human primate, murine, bovine, equine, canine, ovine, or feline.

As used herein, the terms "treat," "treating," "treatment," and the like refer to reducing or ameliorating a disease or condition, e.g., CNS or PNS injury, and/or symptoms associated therewith. Moreover, treatment includes the partial or complete regeneration of nerve fibers in a subject. It will be appreciated that, although not precluded, treating a disease or condition does not require that the disease, condition, or symptoms associated therewith be completely eliminated.

As used herein the term "central nervous system disease, disorder, or condition" refers to any disease, disorder, or trauma that disrupts the normal function or communication of the brain or spinal cord. The CNS and PNS injuries which can be treated according to the present invention are diverse and will be easily understood by the skilled person. Without limitation, there may be mentioned brain and spinal cord injuries due to neurosurgery, trauma, ischemia, hypoxia, neurodegenerative disease, metabolic disorder, infectious disease, compression of the intervertebral disc, tumors, and autoimmune disease.

As used herein, the term "therapeutically active molecule" or "therapeutic agent" means a molecule, group of molecules, complex or substance administered to an organism for diagnostic, therapeutic, preventative medical, or veterinary purposes. This term includes pharmaceuticals, e.g., small molecules, treatments, remedies, biologics, devices, and diagnostics, including preparations useful in clinical screening, prevention, prophylaxis, healing, imaging, therapy, surgery, monitoring, and the like. This term can also specifically include nucleic acids and compounds comprising nucleic acids that produce a bioactive effect, for example In some embodiments, a composition of the invention comprises pharmaceutically active agents. In some embodiments, pharmaceutically active agents are added prior to transplantation. Pharmaceutically active agents include but are not limited to any of the specific examples disclosed herein. Those of ordinary skill in the art will recognize also numerous other compounds that fall within this category and are useful according to the invention. Examples include a growth factor, e.g., nerve growth factor (NGF), brain-derived neurotrophic factor (BDNF), neurotrophic 3 (NT3), or glial cell-line derived neurotrophic factor (GNDF), a steroid, an anti-inflammatory agent, an analgesic agent, a sedative, a peptidic agent, a biopolymeric agent, an antimicrobial agent, an enzyme (e.g., chondroitinase ABC (chABC) or sialidase), a protein, or a nucleic acid. In a further aspect, the pharmaceutically active agent can be steroids such as betamethasone, dexamethasone, methylprednisolone, prednisolone, prednisone, triamcinolone, budesonide, hydrocortisone, and pharmaceutically acceptable hydrocortisone derivatives; non-steroidal antiinflammatory agents, examples of which include but are not limited to sulfides, mesalamine, budesonide, salazopyrin, diclofenac, pharmaceutically acceptable diclofenac salts, nimesulide, naproxene, acetominophen, ibuprofen, ketoprofen and piroxicam, celocoxib, refocoxib, and N-[2-(cyclohexyloxy)-4-nitrophenyl]methanesulfonamide; analgesic agents such as salicylates; sedatives such as benzodiazapines and barbiturates; antimicrobial agents such as penicillins, cephalosporins, and macrolides, including tetracycline, chlortetracycline, bacitracin, neomycin, polymyxin, gramicidin, cephalexin, oxytetracycline, chloramphenicol, rifampicin, ciprofloxacin, tobramycin, gentamycin, erythromycin, penicillin, sulfonamides, sulfadiazine, sulfacetamide, sulfamethizole, sulfisoxazole, nitrofurazone, sodium propionate, minocycline, doxycycline, vancomycin, kanamycin, cephalosporins such as cephalothin, cephapirin, cefazolin, cephalexin, cephardine, cefadroxil, cefamandole, cefoxitin, cefaclor, cefuroxime, cefonicid, ceforanide, cefitaxime, moxalactam, cetizoxime, ceftriaxone, cefoperazone; nucleic acids such as DNA sequences encoding for biological proteins and antisense oligonucleotides; and other pharmacological agents that have been shown to promote axonal regeneration such as paclitaxel (TAXOL®). The term also refers to combinations of any of the therapeutic agents disclosed herein.

As used herein, the term "biological agent," "biological molecule," or "biological therapeutic" is intended to mean a subset of therapeutic agents that are a polypeptide or nucleic acid molecule. In specific embodiments, the biological therapeutic is an agent that induces or enhances nerve growth, e.g., a neurotrophic agent. Examples of useful neurotrophic agents are ocFGF (acidic fibroblast growth factor), FGF (basic FGF), NGF (nerve growth factor), BDNF (brain derived neurotrophic factor), CNTF (ciliary neurotrophic factor), MNGF (motor nerve growth factor), NT-3 (neurotrophin-3), GDNF (glial cell line-derived neurotrophic factor), NT4/5 (neurotrophin4/5), CM101, HSP-27 (heat shock protein-27), IGF-I (insulinlike growth factor), IGF-II (insulin-like growth factor 2), PDGF (platelet derived growth factor) including PDGF-BB and PDGF-AB, ARIA (acetylcholine receptor inducing activity), LIF (leukemia inhibitory factor), VIP (vasoactive intestinal peptide), GGF (glial growth factor), and IL-1 (interleukin-1). In a preferred embodiment, the biological therapeutic is NGF or GNDF. In embodiments, the biological therapeutic is an antibody, antibody fragment, or scFV that induces or enhances nerve growth, e.g., an antibody specific for any of the neurotrophic agents described herein. In other embodiments, the biological therapeutic is a ribozyme, shRNA, or RNAi that induces or enhances nerve growth, e.g., an RNA molecule specific for any of the neurotrophic agents described herein.

As used herein, the term "scaffold" refers to a structure comprising a biocompatible material that provides a surface suitable for adherence/attachment, maturation, differentiation, and proliferation of cells. A scaffold may further provide mechanical stability and support. A scaffold may be in a particular shape or form so as to influence or delimit a three-dimensional shape or form assumed by a population of proliferating cells. All shapes are 3-dimensional and include: films, ribbons, cords, sheets, flat discs, cylinders, spheres, 3-dimensional amorphous shapes, etc.

As used herein, "biocompatible" means the ability of an object to be accepted by and to function in a recipient without eliciting a significant foreign body response (such as, for example, an immune, inflammatory, thrombogenic, or the like response). For example, when used with reference to one or more of the polymeric materials of the invention, biocompatible refers to the ability of the polymeric material (or polymeric materials) to be accepted by and to function in its intended manner in a recipient.

As used herein, "therapeutically effective amount" refers to that amount of a therapeutic agent alone that produces the desired effect (such as treatment of a medical condition such as a disease or the like, or alleviation of a symptom such as pain) in a patient. In some aspects, the phrase refers to an amount of therapeutic agent that, when incorporated into a composition of the invention, provides a preventative effect sufficient to prevent or protect an individual from future medical risk associated with the transplantation procedure. A physician or veterinarian of ordinary skill can readily determine and prescribe the effective amount of the bioactive agent required.

Unless specifically stated or obvious from context, as used herein, the term "about" is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein are modified by the term about.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Culture of Animal Cells—A Manual of Basic Technique" by Freshney, Wiley-Liss, N. Y. (1994), Third Edition; "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference. Other general references are provided throughout this document.

Material and Methods

Cell Culture

Syngeneic cells from the outer layers of postnatal day-7 (P7) ICR strain mice OBs (nerve fiber and glomerular layers) were isolated, as described by Ramon-Cueto, but without purification. Cells were cultured in 2D flasks for 14-17 days, in DMEM/F12 Nutrient Mix+10% fetal bovine serum (FBS; Biological Industries, Beit-Haemek, Israel). To purify OECs, after 14 days in culture the OB-derived cells were sorted by FACSAria flowcytometer to P75NTR negative and p75NTR positive (OECs) cells. After 14 days in-vitro 10% OEC were measured in the unpurified OB-derived cell population. These results are in line with previous report that 11% of the olfactory bulb cells are OECs, 68% are fibroblasts and 21% are astrocytes.

HUVECs (passage 3-7, Clonetics, San Diego, Calif.) were grown on tissue culture plates in EGM-2 medium supplemented with 2% FBS and EGM-2 bullet kit (Cambrex Bio Science, Walkersville). HFF were added to vascularization experiments in order to stabilize the vessels and to improve the vascularization of the engineered tissues, based on their potential to differentiate into smooth muscle cells when co-cultured with endothelial cells (Caspi O, Lesman A, Basevitch Y, Gepstein A, Arbel G, Habib I H, et al. Tissue engineering of vascularized cardiac muscle from human embryonic stem cells. Circulation research. 100:263-72. 2007.). Primary cultures of HFF cells were prepared from newborn foreskin and used until passage 20. HFF cells were cultured in Dulbecco's modified Eagle's medium (DMEM) supplemented with 10% FBS, 1% nonessential amino acids (NEAA) (Biological Industries, Beit-Haemek, Israel), and 0.2% β-mercaptoethanol. PC12 cells (a generous gift from Professor Alon Chen from the Weizmann Institute of Science) were cultured in DMEM supplemented with 8% horse serum and 8% fetal calf serum (FCS) and incubated at 5% $CO_2$ at 37° C. To selectively block of the effect of nerve growth factor (NGF) on PC12 cells (Koizumi S, Contreras M L, Matsuda Y, Hama T, Lazarovici P, Guroff G. K-252a: a specific inhibitor of the action of nerve growth factor on PC12 cells. J Neurosci. 8:715-21. 1988.), the protein kinase inhibitor K252a (200 nM, Sigma) was added to co-cultures of 1:10 PC12 and OB-derived cells or 1:10 PC12 and OECs cells.

Scaffold Preparation

Porous sponges composed of 50% PLLA (Polysciences, Warrington, Pa., USA) and 50% PLGA (Boehringer-Ingelheim, Ingelheim, Germany) were fabricated utilizing a particulate leaching technique to achieve pore sizes of 212-600 μm and 93% porosity. A total of 0.5 g of PLLA and PLGA (50/50), were dissolved in 10 ml chloroform in a small glass tube to yield a solution of 5% polymer (w/v). A 0.24 ml solution of PLLA/PLGA (50/50) was loaded into Teflon cylinders (diameter=21.5 mm, height=25 mm) packed with 0.4 g sodium chloride particles with a sieving range of 212-600 μm. The containers were covered for 1 hr, after which the lids were taken off and the chloroform was evaporated overnight. Scaffolds were removed from their mold and placed in a histology cassette. The cassettes were placed in a 3-4 L beaker filled with distilled water to leach out the salt. Scaffolds were then removed from the cassettes, dried and frozen at −80° C. for at least 12 h prior to lyophilization.

Preparation of 3D Tissue Constructs

PLLA/PLGA (50/50) sponges were sliced into squares (5 mm×5 mm) and placed in 70% ethanol for 1 hr. Scaffolds were then washed in Phospho-buffered saline (PBS) and coated with 20 μg/ml fibronectin (Sigma Aldrich, St. Louis, Mo.) (1 h, room temperature (RT). Prior to seeding, scaffolds were incubated in culture medium for 10 min (RT) and then partially dried using a vacuum. Pelleted cells were resuspended in 5 μl cell culture medium and applied to the scaffolds. After one hour, medium was added and the scaffolds were placed in 37° C. on an XYZ orbital shaker. Medium was replaced every other day throughout the 14- and 28-day culturing periods. For vascularization experiments, cell pellets were resuspended in thrombin (50 NIHU/ml, Sigma Aldrich, St. Louis, Mo.) and then mixed with a fibrinogen solution (20 mg/ml, Sigma Aldrich, St. Louis, Mo.) at a 1:1 ratio. Thrombin was added to convert the soluble fibrinogen into insoluble strands of fibrin. Cells were then added to the scaffolds and incubated at 37° C. for 30 minutes to allow for fibrin clot formation. Culturing medium was then added to the plates and the scaffolds were placed on an XYZ orbital shaker. Medium was replaced every other day throughout the culturing period.

Immunocytochemistry and Confocal Microscopy

Scaffolds were washed twice with PBS and fixed in a solution of 4% PFA and 4% sucrose (30 min, RT). Scaffolds were then washed twice, and treated with 0.3% triton X-100 for 10 min, to permeabilize cells. Following triton treatment, scaffolds were washed with PBS and placed in a blocking solution (10% goat serum and 2% BSA in PBS) for 1 hr. Scaffolds were then incubated (4° C., overnight) with primary antibodies, diluted in blocking buffer. Scaffolds were washed three times with PBS, prior to the incubation with the secondary antibodies (2 hr, RT). Scaffolds were then washed, immersed in PBS and stored at 4° C. until confocal microscopic analysis. Scaffolds were visualized using the LEICA TCS LSI confocal microscope equipped with PLA-NAPO 2.0× and 5.0×/0.50 LWD lenses.

The NGF receptor p75NTR (1:100, Chemicon, Mississauga, Canada) antibody was used to identify and sort OEC. The NGF receptors are highly expressed in PC12 cells and induce their differentiation into neuron-like cells. Thus, both PC12 and OECs were positively stained to p75NTR, as shown in FIG. 3N. To identify differentiated PC12 from OEC we used the specific neuronal marker βIII tubulin antibody (50 μg/ml, Promega, Madison, Wis.). To measure PC12 differentiation, a cell was determined to be positive for neurite extension if it had at least one neurite that was longer than the soma diameter of the cell. TRITC-conjugated Phalloidin (1:250, Sigma-Aldrich, St. Louis, Mo.) was used to stain actin filaments, and DAPI staining (1:1000) was used to visualize cell nuclei. Antibodies were used according to the manufacturers' recommendations.

Real-Time PCR Analysis

RNA was extracted from cells grown on scaffolds or on tissue culture plates using the RNeasy Plus Micro Kit (QIAGEN, Germany), according to manufacturer's protocol. From each experimental and control group, 300 ng of RNA was isolated for real-time analysis using a High Capacity cDNA Reverse Transcription Kit (Applied Biosystems, Foster City, Calif., USA). TaqMan assays were performed using gene expression probes, Mm00443039_m1 for NGF, Mm01334042_m1 for BDNF and Mm 99999915_g1 for GAPDH as a housekeeping control gene (Applied Biosystems, Foster City, Calif., USA). Results were processed using DataAssist Software (Applied Biosystems, Foster City, Calif., USA).

In-Vitro Vascularization Analysis

HUVEC and HFF cells were cultured as previously described (Lesman A, Koffler J, Atlas R, Blinder Y J, Kam Z, Levenberg S. Engineering vessel-like networks within multicellular fibrin-based constructs. Biomaterials. 32:7856-69. 2011). Before seeding, a co-culture of HUVEC and HFF cells was prepared at a ratio of $5 \times 10^5 : 1 \times 10^5$ cells, respectively. In the indicated experiments, the HUVEC/HFF co-culture was resuspended with or without $2 \times 10^5$ OB-derived cells in fibrinogen and thrombin, immediately prior to seeding on PLLA/PLGA scaffolds in equal volumes of HUVEC/HFF/OB culture medium. The suspension was placed on the scaffold and was allowed to be absorbed (1.5 hr, 37° C., 5% $CO_2$), after which 3 ml of multiculture medium composed of equal volumes of HUVEC/HFF/OB culture medium was added and replaced every other day.

Viability and Proliferation Assays

To assess cell viability, scaffolds were loaded with calcein acetoxymethyl ester (calcein AM; 1 μmol/L) and ethidium homodimer-1 (4 μmol/L) (Sigma-Aldrich, St. Louis, Mo.) for 50 minutes at 37° C., on a 3D XYZ shaker. Following dye loading, scaffolds were washed three times with PBS and visualized using a confocal microscope. One group of scaffolds was treated with 0.25% triton x-100 for 1 min prior to the analysis, and served as a positive dead cell control. Metabolic activity was assessed using the Alamar blue assay on scaffolds initially seeded with $2 \times 10^5$ or $5 \times 10^5$ OB cells. The medium surrounding the scaffolds was removed and replenished with medium containing 10% Alamar blue dye (AbD Serotec, Ireland) on days 1, 3, 6, 8, 10 and 13 post-seeding. Constructs were incubated on an orbital shaker for 6 hr. Samples (100 μl) were transferred to a clean spectrophotometer assay plate and absorption was recorded at 570 and 610 nm. The percentage of reduced dye was calculated according to the manufacturer's recommendations.

Example 1

Seeding OB Primary Cultures on PLLA/PLGA Scaffolds

Olfactory bulbs from P7 mice were dissected and used for the preparation of primary cultures. These cultures were initially grown on 2D plates and were then seeded on PLLA/PLGA porous scaffolds. Cells were grown for a period of 28 days and were then fixed and stained with phalloidin-TRITC and p75NTR specific antibody (FIG. 1). By using low magnification microscopy, cell organization around the scaffold's pores was visualized, with few cells residing in the center of the pores (FIG. 1, upper panel). Higher magnification images (lower panel) revealed the organization and interaction between OECs (positively stained for p75NTR) and phalloidin stained cells in the culture.

The results indicated that following multicellular culturing on scaffolds, the OEC marker p75NTR was detected around the scaffold pores (FIG. 1). This cell distribution is unique to the present scaffold. Moreover, the scaffold of the present invention unexpectedly maintained the viability of neuronal cell in-vitro for prolonged periods and managed to support the formation of tissue-like organization within the described artificial settings which are crucial for utilizing the scaffold comprising the cells for implantation procedures. Importantly, the present scaffold unlike previous scaffolds dramatically increases the success rate of in-vivo tissue engineering procedures. The present scaffold maintained the viability of the cells, promoted the formation of thick multicellular constructs in-vitro, promoted tissue organization and cellular maturation, and promoted differentiation due to its capacity in allowing for free penetration of both media and nutrients. Furthermore, as mentioned, the present invention's cell-scaffold arrangements support post-transplantation penetration and viability of regenerated axons and glia from the scaffold and the host spinal cord into the scaffold, where they can then integrate with the transplanted OECs.

Example 2

Cells Grown on Scaffolds Remain Viable and Proliferative

Figure 2:
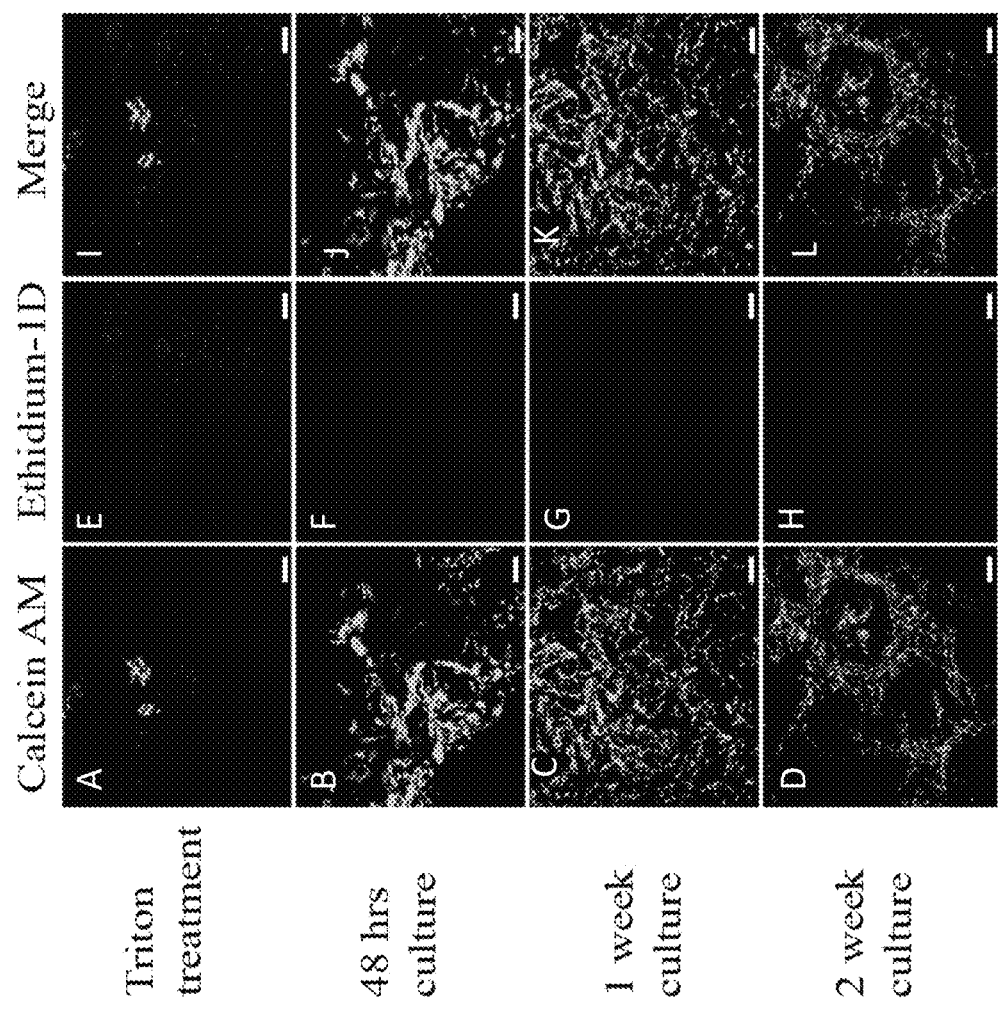
FIG. 2: Micrographs of Viability and proliferation assays of OB-derived cells grown on 3D scaffolds. OB-derived cells grown on PLLA/PLGA scaffolds were subjected to a live/dead assay using the ethidium homodimer (E-H)/calcein AM (A-D) method (gray) and cultured for 48 hr, 1 week or 2 weeks prior to analysis. Merge stainings are in I-L. As negative control, scaffolds were treated with 0.3% triton X-100 for 1 minute prior to the analysis (dark gray). Scale bar=60 µm.
Figure 3:
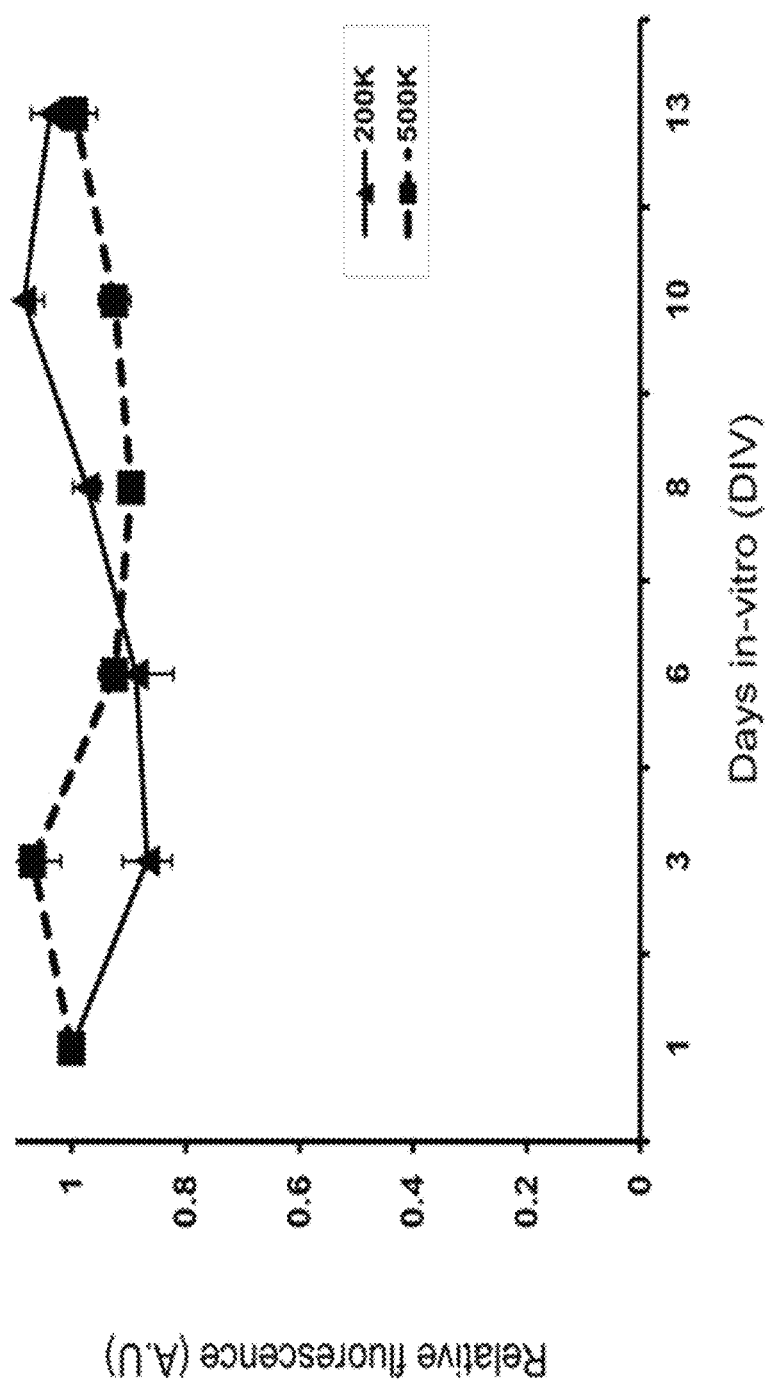
FIG. 3: A graph representing the relative fluorescence of scaffolds seeded with 200,000 or 500,000 OB-derived cells and were subjected to the alamar blue proliferation assay at various time points as indicated (n=3).

In order to analyze the viability of the cells and cell numbers, a live/dead assay and an Alamar Blue assay, were used (FIGS. 2 and 3, respectively). In the live/dead assay, the majority of cells were still viable at two weeks post-seeding (FIG. 2). As a negative control, the cells on the scaffold were treated with Triton X-100, prior to the analysis. In this case, the cells appeared dead, as they were positive for ethidium homodimer (Et-1D) staining. For the quantitative measurement of cell numbers, we used Alamar Blue analysis (FIG. 3). This analysis revealed that the cell numbers initially decreases but then returns to base level after 14-days in culture. Thus the cell viability and proliferation data of the present invention provides that 14 days culturing in-vitro is the minimal culturing period for the OB-derived cell constructs. This period is necessary in order to reach baseline proliferation rates.

Example 3

Figure 4:
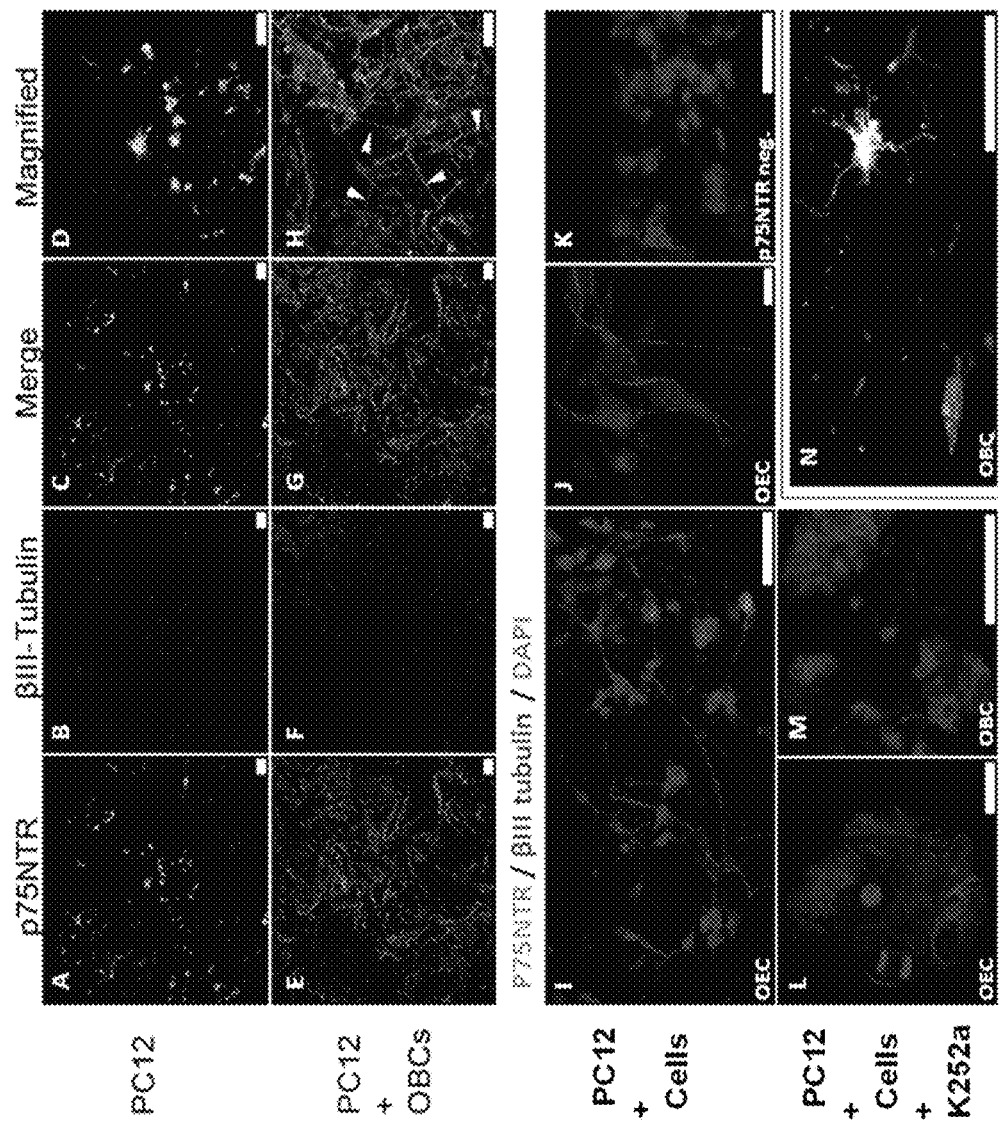
FIG. 4: Micrographs showing that NGF secretion by OEC induces PC12 differentiation on PLLA/PLGA scaffolds. PC12 cells were seeded on PLLA/PLGA scaffolds alone (A-D) or in culture with OEC-containing OB-derived cells (E-H). Co-culture with OB derived cells resulted with robust (>95%) PC12 differentiation, as indicated by µm tubulin staining of long processes emanating from PC12 cells (white arrows). (I, J) Co-culture of purified OB-derived OEC (P75 positive cells) with PC12. OECs are sufficient to induce PC12 differentiation. (K) OB-derived P75NTR negative (OEC-excluded OB-derived cells) culturing with PC12. The absence of OEC in the co-culture resulted in <5% differentiated PC12 cells. When the effect of NGF on PC12 cells was blocked by K252a, >95% of PC12 cells did not exhibit neuronal morphology in culture with OB derived cells (M) or in culture with OECs (L), suggesting blocking of differentiation in most of the PC12 cells. (N) While P75NTR stain both purified OEC and PC12 cells, µm tubulin marks only the PC12 cells. Scale bars (µm): A-H, 60; I, 100; J, 20; K, 100; L, 20; M, 100; N, 50.

OB-Derived Cells Grown on Scaffolds Secrete NGF And Induce Neuronal Differentiation of PC12 Cells It has been previously shown that OECs express and secrete various neurotrophic factors, including NGF, BDNF, and GDNF. To examine whether OEC-containing OB-derived 3D culture affectively secrete NGF, these cells were co-seeded on PLLA/PLGA scaffolds with pheochromocytoma (PC12) cells. PC12 cell line differentiates to a neuronal lineage in response to NGF stimulation, manifested by neuronal phenotype and neuronal genes expression. In this study, differentiation of PC12 cells served as an index for NGF secretion by olfactory bulb cells. To identify PC12 and OECs, the co-culture was stained with P75NTR (expressed by both PC12 and OEC) and βIII-tubulin (mark only PC12), as shown in FIG. 3N. In the absence of OB-derived cells, PC12 cells appeared round, without processes and expressed both p75NTR and βIII-tubulin (FIG. 4A-D). However, when seeded together with OB-derived cells (FIG. 4E-H), PC12 cells took on a neuronal-like morphology with long processes emanating from their cell bodies (FIG. 4H, white arrowheads). PC12 cells acquired similar morphology when cultured only with purified (p75NTR positive cells) OECs (FIG. 4I, J). PC12 differentiation in the presence of OB-derived or OECs was robust and occurred in more than 95% of the cells. Less than 5% of the PC12 cells exhibited the differentiated phenotype in culture with OEC-excluded OB cells (p75NTR negative cells, FIG. 4K). Previous studies have shown that NGF is involved in the induction of PC12 differentiation (Doucette R. Glial cells in the nerve fiber layer of the main olfactory bulb of embryonic and adult mammals. Microsc Res Tech. 24:113-30. 1993). Under the current conditions it was found that the culture medium of OB-derived cells contains secreted NGF (27.6 μg/ml±7.89 SE). To address this, the role of NGF was examined by using K252a which selectively block of the effects of NGF on PC12 cells (Koizumi S, Contreras M L, Matsuda Y, Hama T, Lazarovici P, Guroff G. K-252a: a specific inhibitor of the action of nerve growth factor on PC 12 cells. J Neurosci. 8:715-21. 1988). When K252a was added to the culture medium of PC12 and OB-derived cells (FIG. 3M) or purified OEC (FIG. 4L), more than 95% of PC12 cells did not acquire neuronal-like morphology. Taken together, these results suggest that OECs effectively secrete bioactive growth factors such as NGF to the medium which can effect neuronal differentiation.

Thus the secretion of NGF by OEC was examined, when cultured on 3D environment. After 14 days in culture, in comparison to the 2D cultures, the expression levels of NGF genes were significantly higher. In addition, 3D-cultured OB derived cells and OECs in particular induced robust differentiation of PC12. This effect was blocked when the PC12 response to NGF was selectively inhibited, further demonstrating the critical role of NGF in PC12 differentiation. Taken together, these results demonstrate in-vitro NGF secretion by OECs on PLLA/PLGA 3D scaffolds and offer an advantageous tool for transplantation in spinal cord injury site.

Example 4

Figure 5:
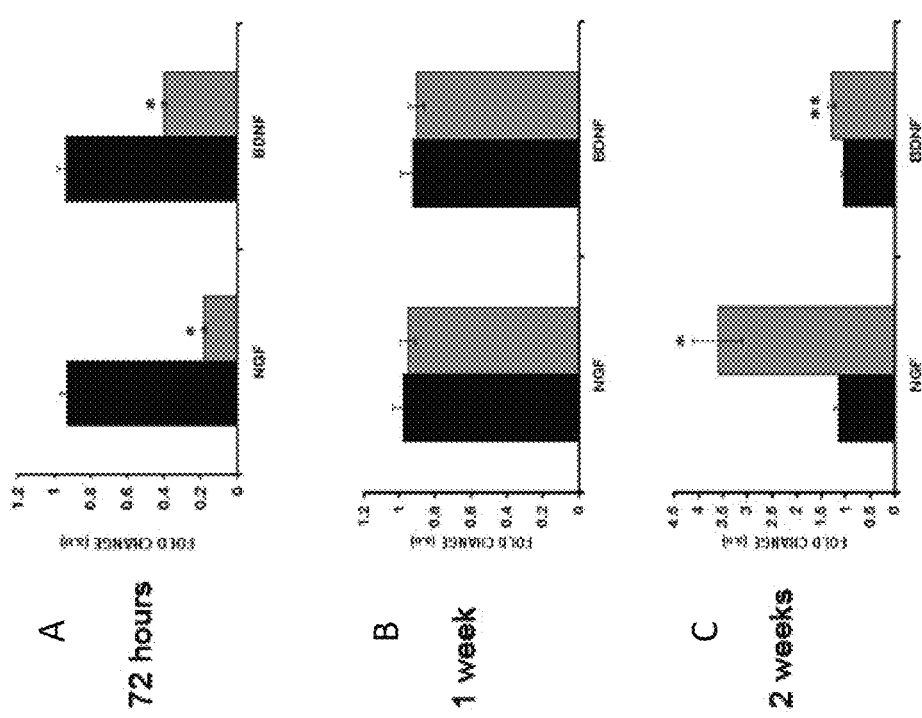
FIG. 5: Graphs (A: 72 hrs, B: 1 week, C: 2 weeks) showing real-time PCR analysis of BDNF and NGF gene expression in OB-derived cells cultured on 2D and 3D scaffolds (the scaffolds of the invention). RNA from OB-derived cells grown either as 2D monolayers (black bars) or on 3D scaffolds (grey bars) was subjected to gene expression analysis at 3 time points: 72 hrs, 1 week and 2 weeks post seeding, n=4, student's t-test * p<0.01, ** p<0.05.

Expression Levels of NGF And BDNF are Dependent on the Culture Spatial and Temporal Organization Quantitative RT-PCR analysis was performed on RNA samples isolated from cells grown on PLLA/PLGA scaffolds and compared to cells grown in a monolayer. At 72 hr post-seeding, cells grown in monolayers exhibited higher levels of both NGF and BDNF when compared to those grown on 3D scaffolds. After one week in culture, similar expression levels of the two genes were measured in both culturing setups. However, when compared to cells grown in 2D monolayers after 14 days, the expression level of NGF and BDNF genes in cells grown on 3D scaffolds was 350% and 30% higher, respectively (FIG. 5).

Example 5

OB-Derived Cells Modulate HUVEC Re-Organization on 3D Scaffolds

Figure 6:
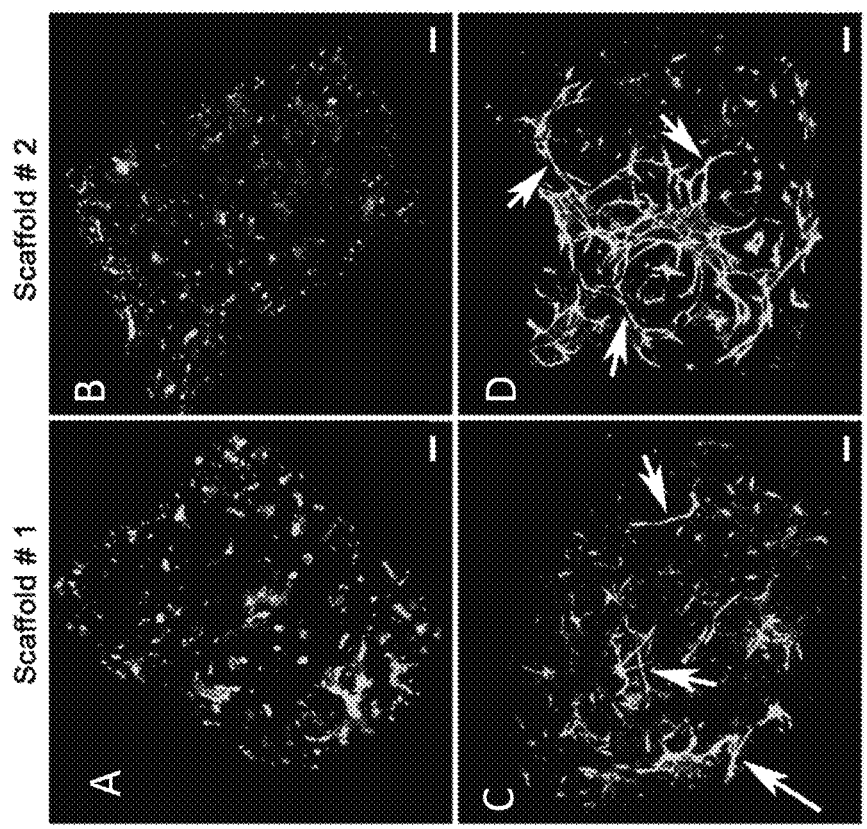
FIG. 6: Micrographs (A-D) show in-vitro vascularization analysis on PLLA/PLGA scaffolds. HUVEC GFP and HFF cells were seeded alone (A, B) or with OB-derived cells (C, D) and cultured for 7 days in HUVEC/HFF/OB medium. Image presents duplicate scaffolds for each experimental group. White arrows indicate endothelial cells rearrangement. Scale bar=300 µm.
Figure 7:
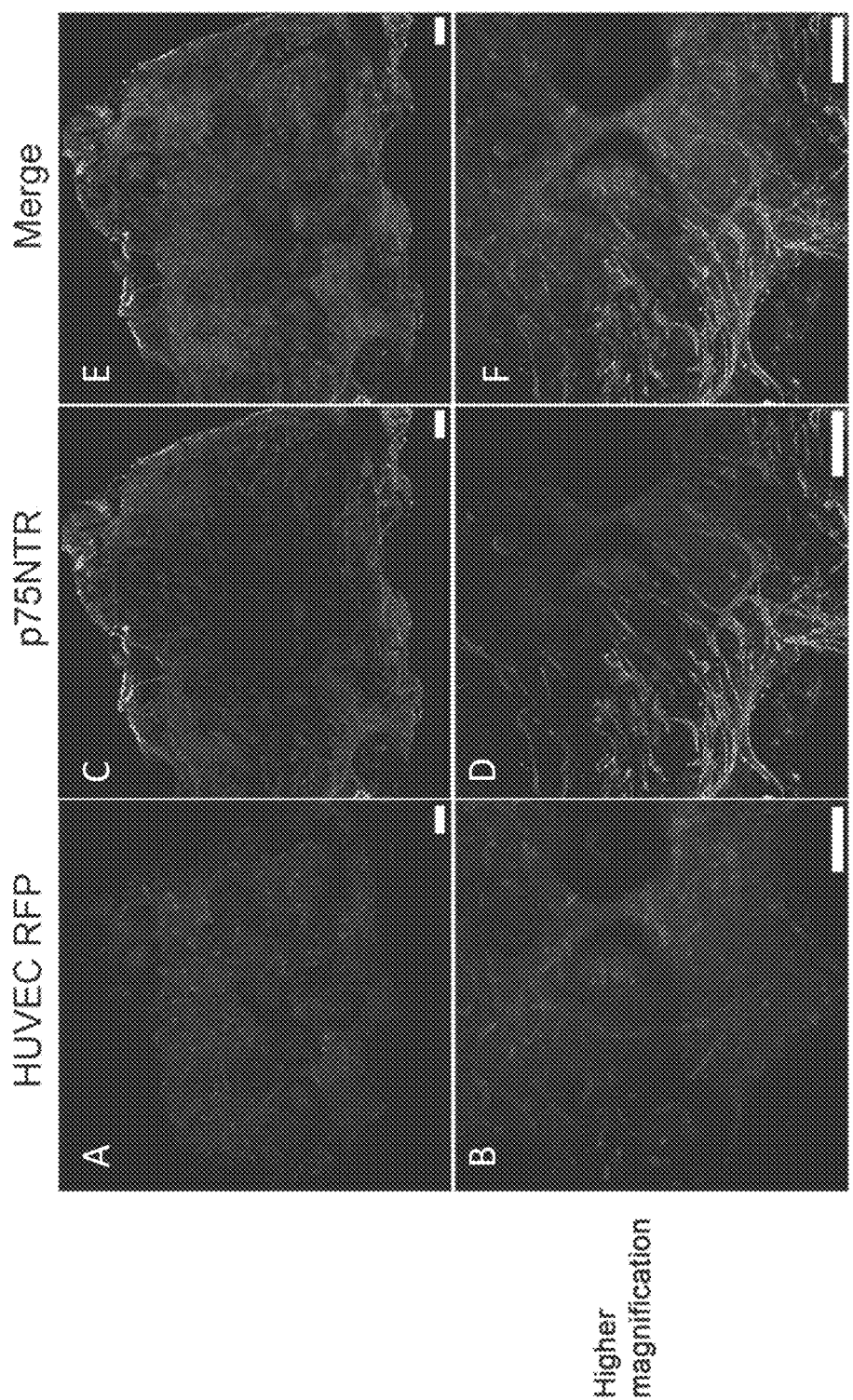
FIG. 7: Are micrographs showing an analysis of distribution of OEC (C and D) and HUVEC (A and B) in PLLA\PLGA scaffolds. E and F are merged distributions. HFF and HUVEC RFP cells were seeded with OB-derived cells on PLLA/PLGA scaffolds. Scale bar=200 µm.

In order to assess the ability of OB-derived cells to promote 3D vascular network formation in-vitro, OB-derived cells were seeded together with HUVEC-GFP and HFF cells on PLLA/PLGA scaffolds and cultured in a medium mix composed of equal volumes of the specific culture medium for each cells (described in "materials and methods"). HUVEC cells cultured in the absence of OB-derived cells remained unorganized (FIG. 6A, B). However, after seven days in culture, in the presence of OB-derived cells, HUVEC-GFP cells organized in an orderly vascular network (FIG. 6C, D). The interaction between OECs and HUVEC cells was also analyzed by staining OECs seeded with HUVEC-RFP and HFF cells on PLLA/PLGA scaffolds, with anti-p75NTR antibodies (FIG. 7). OECs were primarily localized at the periphery of the scaffold, whereas HUVEC cells were homogenously dispersed throughout the entire scaffold.

The present findings showed that OB-derived cells promoted the formation of dense, HUVEC-rich networks of thin vessel-like structures on both PLLA/PLGA and SIS scaffolds (data not shown), further highlighting the supportive features of OB-derived cells for injury repair. These results clearly indicate, for the first time, that OB-derived cells stimulate organization of endothelial cells into de-novo vasculature networks and may explain their ability to attract vascular networks into the spinal cord injury lesion site.

Taken together, the present study demonstrates the feasibility of seeding and culturing OB-derived cells on 3D scaffolds. The 3D scaffold setting dramatically enhanced neurotrophic factors expression, which are suggested to then modulate neuronal survival and differentiation. In addition, OB-derived cells grown on 3D scaffolds supported viability, angiogenic behavior, including formation of endothelial cell-based vessel-like networks. OB-derived cells cultures on 3D PLLA/PLGA scaffolds are ready to be utilized therapeutically and the present findings will enable the design of multi-cellular OB-derived cell-enriched tissues suitable for transplantation in SCI patients.

What is claimed is:

1. An ex-vivo composition, comprising:
   A) a porous sponge comprising poly-l-lactic acid (PLLA), polylactic-co-glycolic-acid (PLGA), and pores having a diameter of from 212 to 600 μm;
   B) culture medium;
   C) olfactory bulb cells and endothelial cells, attached to the surface of said porous sponge and within said porous sponge, said olfactory bulb cells express the NGF receptor p75NTR around said pores;
   D) endogenous nerve growth factor (NGF) produced in-vitro and de-novo by said olfactory bulb cells in said composition, and said NGF is expressed at least 2 fold higher than an NGF expression level in a monolayer of said olfactory bulb cells;
   E) ex-vivo vasculature formed in-vitro within said porous sponge;
   F) fibronectin; and
   G) endogenous brain-derived neurotrophic factor (BDNF) produced in-vitro and de-novo by said olfactory bulb cells in said composition, and BDNF is expressed at a level higher than a BDNF expression level in a monolayer of said olfactory bulb cells, and
   wherein said ex-vivo composition is an ex-vivo vascularized implant.

2. The ex-vivo composition of claim 1, wherein said poly-l-lactic acid (PLLA) and said polylactic-co-glycolic-acid (PLGA) are in 1:1 w/w ratio.

3. The ex-vivo of claim 1, wherein said porous sponge comprises 93% porosity.

4. The ex-vivo composition of claim 1, further comprising foreskin fibroblasts.

5. The ex-vivo composition of claim 1, wherein said porous sponge is coated with fibronectin.

6. The ex-vivo composition of claim 1, wherein said culture medium comprises DMEM/F 12, Nutrient Mix and 10% fetal bovine serum.

7. The ex-vivo of claim 1, further comprising fibrin, thrombin, or both.

8. The ex-vivo composition of claim 1, wherein said olfactory bulb cells comprise cells having a neurite extension.

9. The ex-vivo composition of claim 1, wherein said composition is maintained in-vitro for at least 14 days.

10. An ex-vivo vascularized implant composition, comprising:
    a porous sponge comprising poly-l-lactic acid (PLLA) and polylactic-co-glycolic-acid (PLGA);
    culture medium;
    fibronectin;
    olfactory bulb cells attached to the surface of said porous sponge and within said porous sponge;
    endogenous nerve growth factor (NGF) produced in-vitro and de-novo by said olfactory bulb cells and NGF is expressed at least 2 fold higher than said NGF expression level in a monolayer of said olfactory bulb cells;
    endogenous brain-derived neurotrophic factor (BDNF) produced in-vitro and de-novo by said olfactory bulb cells and BDNF is expressed higher than a BDNF expression level in a monolayer of said olfactory bulb cells; and
    ex-vivo vasculature formed in-vitro within said porous sponge,
    wherein said composition is an ex-vivo vascularized implant.

11. The ex-vivo vascularized implant composition of claim 10, wherein the olfactory bulb cells comprise olfactory bulb derived cells.

12. An ex-vivo vascularized implant composition, comprising:
    a porous sponge comprising poly-l-lactic acid (PLLA) and polylactic-co-glycolic-acid (PLGA);
    culture medium;
    fibronectin;
    olfactory bulb cells attached to the surface of said porous sponge and within said porous sponge;
    endogenous nerve growth factor (NGF) produced in-vitro and de-novo by said olfactory bulb cells;
    endogenous brain-derived neurotrophic factor (BDNF) produced in-vitro and de-novo by said olfactory bulb cells; and
    ex-vivo vasculature formed in-vitro within said porous sponge,
    wherein said ex-vivo composition is an ex-vivo vascularized implant.

13. The ex-vivo vascularized implant composition of claim 12, wherein the olfactory bulb cells comprise olfactory bulb derived cells.

* * * * *